United States Patent
Hu et al.

(10) Patent No.: US 9,023,915 B2
(45) Date of Patent: May 5, 2015

(54) SURFACE TREATMENT OF SILICONE MATERIALS

(71) Applicant: Abbott Medical Optics Inc., Santa Ana, CA (US)

(72) Inventors: Can B. Hu, Irvine, CA (US); Derek D. Pham, Garden Grove, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 125 days.

(21) Appl. No.: 13/834,022

(22) Filed: Mar. 15, 2013

(65) Prior Publication Data

US 2014/0277439 A1    Sep. 18, 2014

(51) Int. Cl.
*G02B 1/04* (2006.01)
*A61L 27/34* (2006.01)
*A61F 2/16* (2006.01)

(52) U.S. Cl.
CPC .............. *G02B 1/043* (2013.01); *A61L 27/34* (2013.01); *A61F 2/16* (2013.01); *A61L 2430/16* (2013.01)

(58) Field of Classification Search
CPC . A61F 2/16; A61F 2/1602; A61F 2002/1697; G02C 7/04; G02C 7/049; G02B 1/043
USPC ...................... 351/159.02; 523/107
See application file for complete search history.

(56) References Cited

U.S. PATENT DOCUMENTS

| | | | |
|---|---|---|---|
| 5,374,663 A | 12/1994 | Daicho et al. | |
| 5,528,322 A | 6/1996 | Jinkerson | |
| 5,543,504 A | 8/1996 | Jinkerson | |
| 5,662,707 A | 9/1997 | Jinkerson | |
| 6,277,940 B1 | 8/2001 | Niwa et al. | |
| 6,310,215 B1 | 10/2001 | Iwamoto | |
| 6,326,448 B1 | 12/2001 | Ojio et al. | |
| 7,033,391 B2 * | 4/2006 | Lai et al. | 623/6.11 |
| 7,071,244 B2 * | 7/2006 | Liao | 523/106 |
| 8,057,906 B2 | 11/2011 | Kashiwagi et al. | |
| 8,075,992 B2 | 12/2011 | Iwamoto et al. | |
| 2007/0197681 A1 | 8/2007 | Lowery et al. | |
| 2009/0088839 A1 | 4/2009 | Hu et al. | |
| 2011/0060408 A1 * | 3/2011 | Tsai et al. | 623/6.32 |

FOREIGN PATENT DOCUMENTS

DE        10123012 C1    7/2002

OTHER PUBLICATIONS

International Search Report and Written Opinion for Application No. PCT/US2014/018593, mailed on Jun. 12, 2014, 7 pages.

* cited by examiner

*Primary Examiner* — Tae H Yoon
(74) *Attorney, Agent, or Firm* — Abbott Medical Optics Inc.

(57) ABSTRACT

Disclosed herein are surface treatments for soft silicone gel materials such as silicone intraocular lenses.

33 Claims, 2 Drawing Sheets

SURFACE TREATMENT OF SILICONE MATERIALS

TECHNICAL FIELD

Disclosed herein are surface treatments for devices that are made from soft silicone materials, such as silicone lenses. The surface treatments may prevent or minimize surface tackiness of the silicone materials, with minimal effect on the optical and mechanical properties of the materials.

BACKGROUND

Soft gel materials are used in various medical device applications, especially in ophthalmologic devices such as intraocular lenses (IOLs) and contact lenses. However, soft materials may exhibit surface tackiness, making the devices difficult to handle and clean. Such materials can also be easily damaged during solvent extraction processes. Methods to prevent or minimize the tackiness of soft gel silicone materials are needed. However, such treatments must not change the optical and mechanical properties of the materials, especially when the materials are used in devices for ophthalmic applications.

SUMMARY

In one aspect, the disclosure is directed to a surface treated intraocular lens, comprising:
a) the product of a reaction mixture comprising a platinum catalyst, a silicon-hydride cross-linker, and a polymer having formula (I):

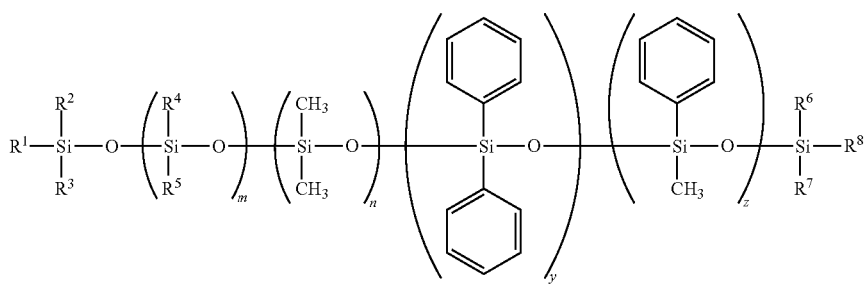

wherein:
the sum of m and n is x;
x is from 0 to about 5000;
y is from 0 to about 500;
z is from 0 to about 500;
the sum of x, y, and z is at least 1;
$R^1$-$R^8$ are each independently selected from the group consisting of hydrogen, —$CH_3$, —$C_6H_5$ and —CH=$CH_2$;
wherein at least one of $R^1$, $R^2$ and $R^3$ is —CH=$CH_2$;
wherein at least one of $R^6$, $R^7$, or $R^8$ is —CH=$CH_2$; and
b) a surface treatment consisting essentially of a compound comprising at least one Si—H bond.

In some embodiments, m is 0 and z is 0. In some embodiments, the polymer has a mole ratio of diphenylsiloxane monomer units of about 0.10 to about 0.20, and a mole ratio of dimethylsiloxane units of about 0.80 to about 0.90. In some embodiments, $R^1$, $R^2$, $R^3$, $R^6$, $R^7$, and $R^8$ are each —CH=$CH_2$. In some embodiments, the cross-linker is selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin, or a mixture of any thereof.

In some embodiments, the surface treatment consists essentially of a compound selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin, or a mixture of any thereof. In some embodiments, the surface treatment consists essentially of a hydride Q resin.

In another aspect, the disclosure is directed to a method for manufacturing a surface treated intraocular lens, comprising:
a) providing a reaction mixture comprising:
(i) a polymer having formula (I):

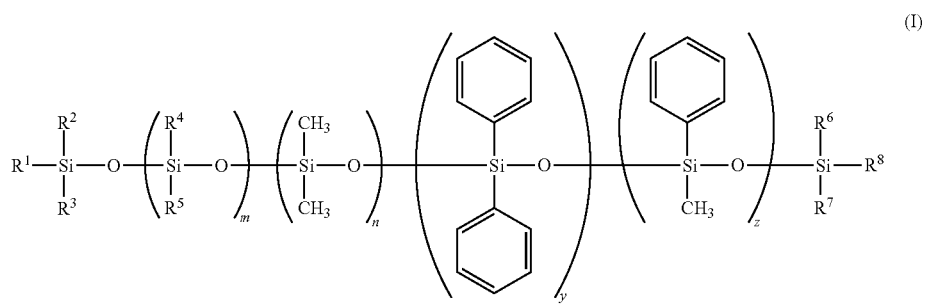

wherein:
the sum of m and n is x;
x is from 0 to about 500;
y is from 0 to about 500;
z is from 0 to about 500;
the sum of x, y, and z is at least 1;
$R^1$-$R^8$ are each independently selected from the group consisting of hydrogen, —$CH_3$, —$C_6H_5$ and —CH=$CH_2$;
wherein at least one of $R^1$, $R^2$ and $R^3$ is —CH=$CH_2$;
wherein at least one of $R^6$, $R^7$, or $R^8$ is —CH=$CH_2$;
(ii) a silicon hydride cross-linker; and
(iii) a platinum catalyst;
b) curing the reaction mixture to provide a cured silicone material;
c) surface treating the cured silicone material with a surface treatment composition consisting essentially of a compound comprising at least one Si—H bond to provide a surface treated silicone material; and
d) drying the surface treated silicone material to provide the surface treated intraocular lens.

In some embodiments, m is 0 and z is 0. In some embodiments, the polymer has a mole ratio of diphenylsiloxane monomer units of about 0.10 to about 0.20, and a mole ratio of dimethylsiloxane units of about 0.80 to about 0.90. In some embodiments, $R^1$, $R^2$, $R^3$, $R^6$, $R^7$, and $R^8$ are each —CH=$CH_2$. In some embodiments, the cross-linker is selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin, or a mixture of any thereof. In some embodiments, the surface treatment composition consists essentially of a compound selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin, or a mixture of any thereof. In some embodiments, the surface treatment composition consists essentially of a hydride Q resin.

In some embodiments, the surface treating step comprises contacting the cured silicone material with the surface treatment composition for about 10 seconds to about 10 minutes. In some embodiments, the drying step comprises drying the surface treated silicone material for about 1 minute to about 60 minutes. In some embodiments, the surface treated silicone material is dried at a temperature of about 100° C. to about 180° C. In some embodiments, the method further comprises a step of extracting the cured silicone product with an organic solvent, after step d). In some embodiments, the extracting step comprises Soxhlet extraction. In some embodiments, the organic solvent is selected from the group consisting of ethanol and isopropanol.

In another aspect, the disclosure is directed to an intraocular lens prepared by a process comprising the steps of:
a) providing a reaction mixture comprising:
(i) a polymer having formula (I):

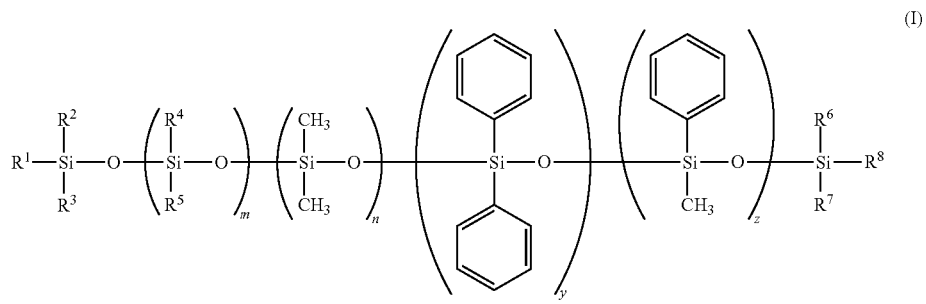

(I)

wherein:
the sum of m and n is x;
x is from 0 to about 5000;
y is from 0 to about 500;
z is from 0 to about 500;
the sum of x, y, and z is at least 1;
$R^1$-$R^8$ are each independently selected from the group consisting of hydrogen, —$CH_3$, —$C_6H_5$ and —CH=$CH_2$;
wherein at least one of $R^1$, $R^2$ and $R^3$ is —CH=$CH_2$;
wherein at least one of $R^6$, $R^7$, or $R^8$ is —CH=$CH_2$;
(ii) a silicon hydride cross-linker; and
(iii) a platinum catalyst;
b) curing the reaction mixture to provide a cured silicone material;
c) surface treating the cured silicone material with a surface treatment composition consisting essentially of a compound comprising at least one Si—H bond to provide a surface treated silicone material; and
d) drying the surface treated silicone material.

In some embodiments, m is 0 and z is 0. In some embodiments, the polymer has a mole ratio of diphenylsiloxane monomer units of about 0.10 to about 0.20, and a mole ratio of dimethylsiloxane units of about 0.80 to about 0.90. In some embodiments, $R^1$, $R^2$, $R^3$, $R^6$, $R^7$, and $R^8$ are each —CH=$CH_2$. In some embodiments, the cross-linker is selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin, or a mixture of any thereof. In some embodiments, the surface treatment composition consists essentially of a compound selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin, or a mixture of any thereof. In some embodiments, the surface treatment composition consists essentially of a hydride Q resin.

In some embodiments, the surface treating step comprises contacting the cured silicone material with the surface treatment composition for about 10 seconds to about 10 minutes. In some embodiments, drying step comprises drying the surface treated silicone material for about 1 minute to about 60 minutes. In some embodiments, the surface treated silicone material is dried at a temperature of about 100° C. to about 180° C. In some embodiments, the method further comprises a step of extracting the surface treated silicone material with an organic solvent, after step d). In some embodiments, the extracting step comprises Soxhlet extraction. In some embodiments, the organic solvent is selected from the group consisting of ethanol and isopropanol.

Other aspects and embodiments will become apparent in light of the following description and drawings.

DETAILED DESCRIPTION

Figure 1:
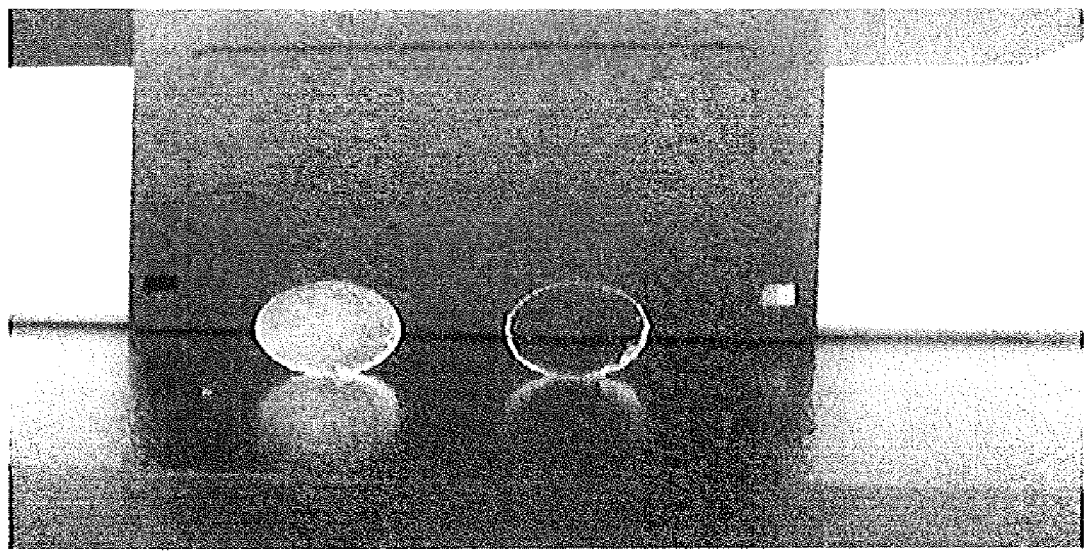
FIG. 1 shows an image of silicone discs following Soxhlet extraction, wherein the discs are without (left) and with (right) a surface treatment as described herein.

Described herein are surface treated soft silicone materials and methods for treating the surfaces of soft silicone materials, which can harden the surfaces of the materials with minimal effect on the optical and mechanical properties of the original materials. The surface treatments may be particularly useful for medical devices for which the optical properties are of great importance, such as IOLs. The surface-treated IOLs may have surfaces with reduced tackiness, and can also resist damage during solvent extraction processes.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

Elongation: As used herein, "elongation" refers to the act of lengthening or stretching a polymeric material. In some instances, the elongation may be represented by the following formula where L is the length of the elongated polymer and $L_0$ is the length of the corresponding non-elongated polymer: $[L/L_0]$ Full Elongation: As used herein, "full elongation" refers to the act of lengthening or stretching a polymeric material or polymeric IOL to its elastic limit.

Intermediate Elongation: As used herein, "intermediate elongation" refers to the act of lengthening or stretching a polymeric material or polymeric IOL to a point between its original length and limit.

Glass Transition Temperature ($T_g$): As used herein, the "glass transition temperature ($T_g$)" refers to the temperature wherein a polymeric material becomes less elastic and more brittle.

Compression Modulus or Modulus of Elasticity: As used herein "modulus of elasticity" refers to the ratio of stress to strain. As used herein, "compression modulus" refers to the ratio of compressive stress to compressive strain.

Moduli: As used herein, "moduli" refers to the plural form of modulus or modulus of elasticity.

Molar Ratio: As used herein, "molar ratio" refers to the moles of each monomer divided by the total moles of all monomers in the formulation.

Percent Elongation: As used herein, "percent elongation" refers to the length of an elongated polymer divided by the length of the original polymer. Mathematically, the percent elongation is represented by the following formula where L is the length of the elongated polymer and $L_0$ is the length of the corresponding non-elongated polymer: $[L/L_0] \times 100 =$ Percent Elongation.

Pliable: As used herein, "pliable" refers to the flexible nature of a polymeric material and to the flexibility of polymeric IOLs that can be folded, rolled or otherwise deformed sufficiently to be inserted through a 2 mm or less surgical incision.

kPa: As used herein, "kPa" refers to kilopascal, which is a unit of pressure or stress and is the equal to 1000×Newton per meter squared ($N/m^2$).

Resiliency: As used herein, "resiliency" refers to a polymeric material's or a polymeric IOL's inherent ability to return to its unstressed configuration following impact, deformation in an inserter, or the resulting deformation associated with the stress on impact, also referred to herein after as "rebound resiliency."

Refractive Index (RI): As used herein, "refractive index (RI)" refers to a measurement of the refraction of light of a material or object, such as an IOL. More specifically, it is a measurement of the ratio of the speed of light in a vacuum or reference medium to the speed of light in the medium of a substance, material, or device under examination. The refractive index of a substance, material, or device typically varies with the wavelength of the light, a phenomenon sometimes referred to as dispersion.

Softness: As used herein, "softness" refers to a polymeric material's or a polymeric IOL's pliability as opposed to, for example, a polymethylmethacrylate (PMMA) IOL that is rigid and hard.

Ultimate Tensile Strength: As used herein, "ultimate tensile strength" refers to the maximum stress a material can withstand before fracture and is measured in psi (lb/in$^2$).

Clear Aperture: As used herein, "clear aperture" refers to the portion of an optic that limits the extent of the rays from an object that contributes to the conjugate image and is generally expressed as a diameter of a circle.

Common Polymeric Material: As used herein, "common polymeric material" refers to similarity of material composition between two objects or portions of an object. Two objects or portions of an object comprise a common polymeric material if the two objects or portions consist essentially of the same base polymer chain or have at least 50% w/w of the same base polymer chain, or 75% w/w of the same base polymer chain, or 85% w/w of the same base polymer chain, or 90% w/w of the same base polymer chain, or 95% w/w of the same base polymer chain, and, when present, the same cross-linking agent.

Common Refractive Index: As used herein, "common refractive index" refers to the similarity of refractive indices between two materials. A common refractive index between two materials would be a difference in refractive index between the two materials of less than or equal to 1% at a predetermined wavelength in the visible light waveband.

Hydride Q Resin: As used herein, a "hydride Q resin" refers to a compound having a Chemical Abstracts Service (CAS) Registry Number of 68988-57-8.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Surface-Treated Silicone Materials

The surface-treated silicone materials described herein include a cured silicone gel material that is surface-treated with a silicon-hydride compound. The surface treatment may protect the silicone material from potential damage during extraction processes and may improve the surface properties of the material, e.g., by reducing surface tackiness. Importantly, the surface treatment may not alter the refractive index of the material, making it suitable for use in applications such as intraocular lenses or contact lenses.

a. Silicone Gel Materials

The cured silicone gel materials can be prepared using conventional methods, namely curing a reaction mixture comprising a silicone polymer (e.g., a polymer of formula (I) described herein) with a silicon hydride cross-linker and a platinum catalyst. The silicone materials may therefore be the reaction product of the silicone polymer (e.g., a polymer of formula (I) described herein), the silicon hydride cross-linker, the platinum catalyst, and optional additional components such as initiators, antioxidants and/or dyes. The silicone materials can be prepared using a method comprising: providing a silicone polymer (e.g., a polymer of formula (I) described herein); providing a silicon hydride cross-linker; providing a catalyst; combining the polymer, cross-linker and catalyst to form a mixture; and curing the mixture to provide the silicone material.

(1) Polymers

In some embodiments, the silicone polymers may have the following formula (I):

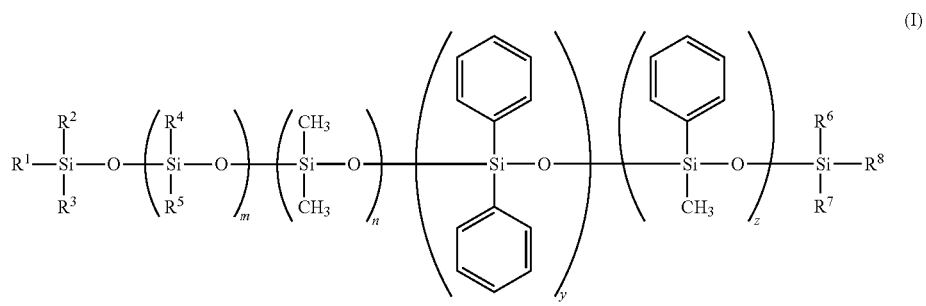

wherein:

the sum of m and n is x;

x is from 0 to about 5000;

y is from 0 to about 500;

z is from 0 to about 500;

the sum of x, y, and z is at least 1;

$R^1$-$R^8$ are each independently selected from the group consisting of hydrogen, —$CH_3$, —$C_6H_5$ and —CH=$CH_2$;

wherein at least one of $R^1$, $R^2$ and $R^3$ is —CH=$CH_2$; and wherein at least one of $R^6$, $R^7$, or $R^8$ is —CH=$CH_2$.

It will be understood by the skilled artisan that while the polymer of formula (I) is drawn as a block copolymer, the polymers of formula (I) are random copolymers of the monomer units indicated within the parentheses. For example, when in is 0, the polymers of formula (I) may represent random copolymers of dimethylsiloxane, diphenylsiloxane, and methylphenylsiloxane monomer units. Because at least one of $R^1$, $R^2$ and $R^3$ is —CH=$CH_2$ and at least one of $R^6$, $R^7$, or $R^8$ is —CH=$CH_2$, the polymer is divinyl, trivinyl, tetravinyl, pentavinyl or hexavinyl siloxy terminated.

In some embodiments, at least two of $R^1$, $R^2$ and $R^3$ are —CH=$CH_2$. In some embodiments, at least two of $R^6$, $R^7$, or $R^8$ are —CH=$CH_2$. In some embodiments, at least two of $R^1$, $R^2$ and $R^3$ are —CH=$CH_2$ and at least two of $R^6$, $R^7$, or $R^8$ are —CH=$CH_2$. (In other words, the polymer is tetravinyl terminated.) In some embodiments, each of $R^1$, $R^2$, $R^3$, $R^6$, $R^7$ and $R^8$ is —CH=$CH_2$. (In other words, the polymer is hexavinyl terminated.)

In some embodiments, the silicone polymers may have the following formula (II):

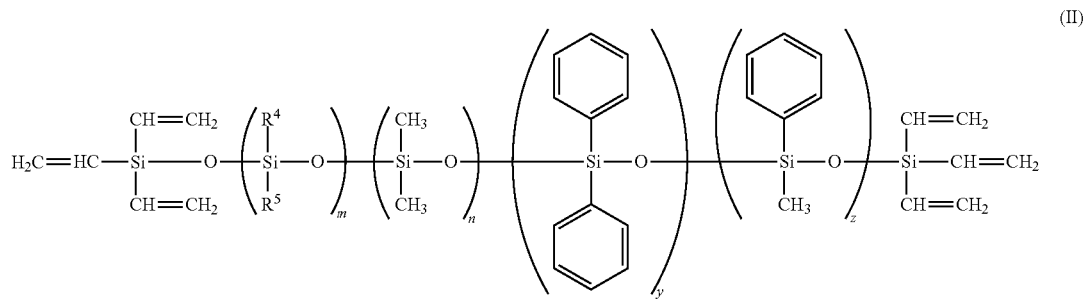

wherein:
the sum of m and n is x;
x is from 0 to about 5000;
y is from 0 to about 500;
z is from 0 to about 500; and
the sum of x, y, and z is at least 1.

In some embodiments of formula (I) or formula (II), the sum of m and n is x. In some embodiments, m is 0. In some embodiments, x is 0, or x is about 100, 100, 200, 300, 400, 500, 600, 700, 800, 900, 1000, 1500, 2000, 2500, 3000, 3500, 4000, 4500 or 5000. In some embodiments, y is 0, or y is about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500. In some embodiments, z is 0, or z is about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500.

In some embodiments of formula (I) or formula (II), the sum of the molar ratios of the monomers shown in the parentheses with subscripts m, n, y and z (i.e. $-Si(R^4)(R^5)O-$, $-Si(CH_3)_2O-$, $-Si(C_6H_5)_2O-$ and $-Si(C_6H_5)(CH_3)O-$) is 1.0. In some embodiments, the mole ratio of the monomers having the formula $-Si(R^4)(R^5)O-$ is 0 to about 0.01, e.g., about 0 or about 0.01. In some embodiments, the mole ratio of the monomers having the formula $-Si(CH_3)_2O-$ (i.e. dimethylsiloxane) is about 0.6 to about 0.9, e.g., about 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, or 0.90. In some embodiments, the mole ratio of the monomers having the formula $-Si(C_6H_5)_2O-$ (i.e. diphenylsiloxane) is about 0.07 to 0.55, e.g., about 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, or 0.55. In some embodiments, the mole ratio of the monomers having the formula $-Si(C_6H_5)(CH_3)O-$ (i.e. methylphenylsiloxane) is 0 to about 0.9, e.g., 0, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, or 0.90.

The degree of polymerization of the polymers of formula (I) or formula (II) may be from about 200 to about 1000, e.g., about 500 to about 1000, or about 500 to about 800. For example, the degree of polymerization may be about 200, 250, 300, 350, 400, 450, 500, 550, 600, 650, 700, 750, 800, 850, 900, 950 or 1000.

The refractive index of the silicone polymers of formula (I) or formula (II) may be from about 1.40 to about 1.56, or from about 1.41 to about 1.52. For example, the refractive index may be about 1.40, 1.41, 1.42, 1.43, 1.44, 1.45, 1.46, 1.47, 1.48, 1.49, 1.50, 1.51, 1.52, 1.53, 1.54, 1.55 or 1.56.

(2) Cross-Linkers

The cross-linkers include silicon-hydride cross-linkers, such as compounds having at least two Si—H bonds. Exemplary hydride-containing cross-linkers include, but are not limited to: nonpolymeric cross-linkers such as phenyltris (dimethylsiloxy)silane (Formula 3 below), tetrakis(dimethylsiloxy)silane (Formula 4 below), 1,1,3,3-tetraisopropyldisiloxane, 1,1,3,3-tetramethyldisiloxane, 1,1,4,4-tetramethyldisilethane bis(dimethylsilyl)ethane and 1,1,3,3-tetramethyldisilazane; hydride terminated polymeric cross-linkers with different molecular weights, such as hydride-terminated polydimethylsiloxanes (Formula 5 below, wherein q is about 2 to about 1000) including DMS-H03, DMS-H11, DMS-H21, DMS-H25, DMS-H31 and DMS-H41 commercially available from Gelest, hydride terminated polyphenyl-(di-methylhydrosiloxy)siloxanes (Formula 6 below, wherein w is about 5 to about 50) such as HDP-111 commercially available from Gelest, and hydride terminated methylhydrosiloxane-phenylmethylsiloxane copolymers, such as HPM-502 commercially available from Gelest; non-hydride terminated polymeric cross-linkers such as trimethylsiloxy terminated-polymethylhydrosiloxanes and trimethylsiloxy-terminated methylhydrosiloxane-dimethylsiloxane copolymers, such as XL-103, XL-110, XL-111, XL-112, XL-115 and XL-150 commercially available from NuSil, and HMS-013, HMS-031, HMS-082, HMS-151, HMS-301, HMS-991 commercially available from Gelest.

Formula 3

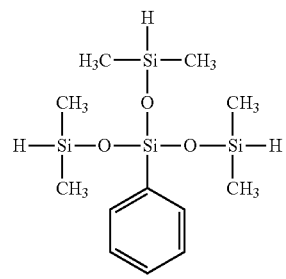

Phenyltris(dimethylsiloxy)silane

-continued

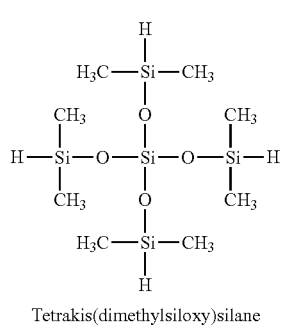

Tetrakis(dimethylsiloxy)silane

Formula 4

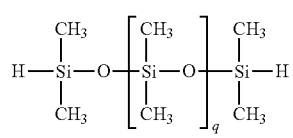

Hydride-terminated Polydimethylsiloxanes

Formula 5

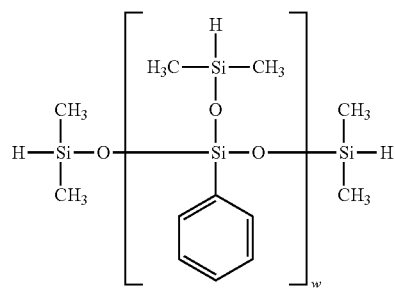

Hydride-terminated Polyphenyl-(di-methylhydrosiloxy)siloxane

Formula 6

Other Si—H containing compounds may also be used. For example, suitable Si—H containing compounds are known as Hydride Q resins, CAS No. 68988-57-8, also known as "Silicic acid ($H_4SiO_4$), tetraethyl ester, reaction products with chlorodimethylsilane". Such compounds are commercially available from Gelest as HQM-105 and HQM-107, illustrated as having the following formula:

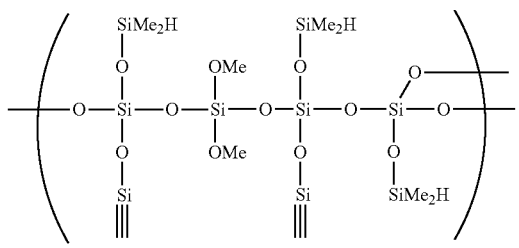

Hydride Q resins commercially available from Gelest, as HQM-105 and HQM-107, may have a viscosity of from 3-8 cSt. (e.g., 3-5 cSt. for HQM-105 and 6-8 cSt. for HQM-107), a hydride equivalent/kilogram of 7.5-9.2 (e.g., 7.8-9.2 for HQM-105 and 7.5-9.0 for HQM-107), an equivalent weight of 110-135 (e.g., 110-130 for HQM-105 and 115-135 for HQM-107), a specific gravity of about 0.90 to about 1.0 (e.g., 0.94 for HQM-105 and 0.95 for HQM-107), and a refractive index of 1.41.

(3) Catalysts

The catalyst may be, for example, a platinum catalyst. Exemplary platinum catalysts include but are not limited to platinum-tetravinyltetramethylcyclotetrasiloxane complex, platinum carbonyl cyclovinylmethylsiloxane complex, platinum cyclovinylmethylsiloxane complex, and platinum octanaldehyde/octanol complex. Many different platinum catalysts may be used depending on, inter alia, the desired pot life. The platinum catalyst can be used in amounts by weight of at least about 0.01%, at least about 0.05%, or at least about 0.1%. Suitably, the platinum catalyst is used in amounts of about 1% or less, more preferably about 0.75% or less, about 0.5% or less, about 0.4%, about 0.3%, about 0.2%, about 0.1% or about 0.05% by weight.

In addition to platinum catalysts, other metal catalysts can be used. In some embodiments, transition metals can be used as catalysts, more specifically, palladium and rhodium catalysts can be used. Complexes and salts of metal catalysts can be used. An example of a transition metal complex used as a catalyst is tris(dibutylsulfide) rhodium trichloride.

In certain embodiments, the platinum catalyst level for a polymer may be increased to levels significantly higher than conventionally used (e.g., up to 50 ppm versus a more traditional 10 ppm or less). A skilled artisan may expect that as catalyst concentration increases, curing time may decrease and polymer cross-linking may increase. The skilled artisan may also expect this to lead to a more rigid or firm polymer (even assuming curing temperature may be the same). In certain embodiments, the catalyst may be increased to atypical levels and a significant decrease in curing time may be observed.

(4) Additional Components

The reaction mixture for producing the silicone materials may optionally comprise additional components, including but not limited to dyes, initiators, antioxidants and methylvinyl cyclics ("MVCs"). Additionally, the properties of the silicone materials may be adjusted by varying the amounts of the components.

Optionally, a number of ultraviolet (UV) and blue light absorbing dyes can be added to the silicone polymers. For example, the silicone IOLs may include 0.1 to 1.5 mass % of UV and blue light absorbing compounds such as benzophenone and benzotriazole-based UV light absorbers or blue light blocking dyes including azo and methine yellow, which selectively absorb UV/blue light radiation up to about 450λ. See, for example, U.S. Pat. Nos. 5,374,663, 5,528,322, 5,543,504, 5,662,707, 6,277,940, 6,310,215 and 6,326,448, the entire contents of which are incorporated herein by reference. Other UV absorbers include Tinuvin® 326 (2-(5-chloro-2H-benzotriazole-2-yl)-6-(1,1-di-methylethyl)-4-methylphenol), UVAM (2-(3'-tert-butyl-2'-hydroxy-5'-vinyl-phenyl)-5-chlorobenzotriazole), oMTP (2-(2H-benzo[d][1,2,3]triazol-2-yl)-6-(but-3-en-1-yl)-4-methylphenol), 2-(4-benzoyl-3-hydroxyphenoxy)ethyl acrylate, and UV absorbers from Adesis, Inc. including Adesis 16-100 (3-(3-(tert-butyl)-5-(5-chloro-2H-benzo[d][1,2,3]triazol-2-yl)-4-hydroxyphenyl) propyl methacrylate), Adesis 16-101 (2-(tert-butyl)-4-(3-(dimethyl(vinyl)silyl)propoxy)-6-(5-methoxy-2H-benzo[d][1,2,3]triazol-2-yl)phenol), Adesis 16-102 (2-(3-(tert-butyl)-4-hydroxy-5-(5-methoxy-2H-benzo[d][1,2,3]triazol-2-yl) phenoxy)ethyl methacrylate) and Adesis 16-103 (3-(3-(tert-butyl)-4-hydroxy-5-(5-methoxy-2H-benzo[d][1,2,3]triazol-2-yl)phenoxy)propyl methacrylate).

A variety of initiators for polymerization reactions can be employed. In one non-limiting embodiment, peroxide initiators are used. Examples of peroxide initiators include, without limitation, about 0.100 to about 1.50 mass % of di-test-butyl peroxide (Trigonox® a registered trademark of Akzo Chemie Nederland B.V. Corporation Amersfoort, Netherlands) or 2,5-dimethyl-2,5-bis(2-ethylhexanoylperoxy)hexane. It should be noted that peroxide initiators can initiate the cross-linking of vinyl groups on monomers (e.g., those on vinyl-terminated silicone monomers). While this can help facilitate the cross-linking of the silicone monomers, at least some of the hydride groups must still be cross-linked.

In certain embodiments, the reaction mixture may comprise one or more methyl-vinyl cyclics ("MVCs"). In certain embodiments, the presence or amount of MVCs as well as the amount of catalyst may affect the modulus of material. For example, in certain embodiments, as the amount of catalyst and/or MVCs is increased, the modulus of the material may also increase until a peak modulus is reached. In certain embodiments, after a peak modulus is reached, the modulus may begin to level off or, in some cases, may decrease.

In certain embodiments, the MVC may be any methylvinyl siloxane, which includes cyclosiloxane and non-cyclosiloxane classes of materials. Non-limiting examples of methylvinyl cyclosiloxane classes include tetramethylvinylcyclotetrasiloxane and pentamethylvinyleyclopentasiloxane. Non-cyclosiloxane classes include 1,3-tetramethyldisiloxane, divinyltetraphenyldisiloxane, 1,5-divinylhexamethyltrisiloxane, and 1,5-divinyl-3,3-diphenyltetramethyltrisiloxane. One example of an MVC is 1,3,5,7-tetravinyl-1,3,5,7-tetramethylcyclotetrasiloxane. In certain embodiments, the MVC may be present in an amount of at least about 0.01% or at most about 1% by weight. It should be understood that for certain polymer embodiments described herein, MVCs may partially substitute the catalyst, augment the catalyst or be used to alter the 1-1/V ratio. The MVC, in certain embodiments, may have an inversely proportional impact on the moduli of polymers prepared therewith.

For certain embodiments and without wishing to be bound by theory, one reason for the impact of some catalysts, especially platinum catalysts, on the modulus may be due to the presence of an inhibitor or stabilizer that may reduce the hydride/vinyl ratio and/or may prevent complete curing. An example of such an agent may be an MVC such as cyclovinylmethylsiloxane (e.g., 1,3,5,7-tetravinyl-1,3,5,7-tetramethylcyclotetrasiloxane). It is worthwhile to note that in certain embodiments, the effects of catalyst amounts on modulus may be independent of curing time. While MVCs may sometimes be used as stabilizers in catalysts to, for example, keep platinum suspended in solution, the MVCs may be present in such small amounts that they may be inert.

In certain embodiments, the resulting polymer may be far less rigid and less firm than expected. In certain embodiments, excessive amounts of catalyst may be used and the corresponding increase in MVCs may allow them to become reactive ingredients and may end-cap the hydrides on the cross-linkers, which may result in more free ends on the structural polymers. The additional free ends may provide a less-cross-linked and, therefore, less rigid polymer. As a skilled artisan will appreciate, in certain embodiments, such a polymer may be ideal for preparing many products including, but not limited to, products implantable in patients (e.g., IOLs, augmentation implants).

In certain embodiments, the MVC may be present in an amount of at least about 0.01%, about 0.05%, about 0.1%, about 0.11%, about 0.15%, about 0.2%, or about 0.25% by weight; to at most about 1%, about 0.75%, about 0.5%, about 0.4%, about 0.39%, about 0.35%, or about 0.35% by weight. In certain embodiments, the MVCs may partially substitute the catalyst in any proportion or amount including completely or the MVC may augment the catalyst. In certain embodiments, the MVC may have an inversely proportional impact on the moduli of polymers prepared therewith. Certain embodiments described herein may incorporate the teachings regarding MVCs and their relationship to the moduli of polymer articles prepared therefrom.

(5) Methods of Making Silicone Materials

The silicone materials may be prepared, for example, using a method comprising several steps. For example, the method may comprise a step of providing a reaction mixture comprising the polymer having formula (I), the cross-linker, and the platinum catalyst as described above and herein. The method may then further comprise the steps of pouring the reaction mixture into a mold, curing the reaction mixture to provide a cured silicone material, and drying the silicone material.

The method may further comprise the step of pouring the reaction mixture into a mold. The mold may be made of any suitable material, such as metal, Teflon, or the like.

The method further comprises the step of curing the reaction mixture to provide the cured silicone material. The curing may take place at ambient temperature or at elevated temperature. For example, the curing step may be conducted at about 20° C. to about 200° C., e.g., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., or about 200° C. The curing may be conducted for about 1 minute to about 60 minutes, e.g. about 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, or 60 min.

Properties of the silicone materials such as modulus, percent weight loss may be changed by varying the ratio of hydride and vinyl contents (H/V ratio) in the silicone fluids. Vinyl content of a silicone fluid may be determined by, for example, the GPC method, titration, or NMR (nuclear magnetic resonance spectroscopy). By varying the ratio of hydride primarily from the cross-linker and vinyl primarily from the vinyl silicone fluid, silicone materials with different moduli may be obtained. In certain embodiments, the H/V ratio may be at least about 0.1, at least about 0.5, about 0.6, about 0.7, about 0.8, about 0.9, about 1.0, about 1.1, about 1.25, or at most about 1.5.

Following curing, the silicone material may be subjected to one or more optional steps such as rinsing, drying, extraction, and the like. The silicone material may then be surface treated as described below.

b. Surface Treatment Compositions

The silicone materials described herein are further treated with a surface treatment composition consisting essentially of a compound comprising at least one silicon-hydrogen bond. As used herein, the term "consisting essentially of" means that the surface treatment composition includes the compound comprising at least one silicon-hydrogen bond, and does not include further compounds that would affect the basic and novel properties of the surface treatment composition. For example, the surface treatment composition may further comprise water and/or one or more solvents (as described further below and herein), and may further include a catalyst such as a platinum catalyst to facilitate further cross-linking between the silicon-hydride compound and the silicone material. The surface treatment composition may not include any vinyl-containing silicone polymers. The surface treatment composition may additionally not include any compounds that would alter the optical properties of the silicone material, such as the refractive index.

The surface treatment composition consists essentially of a compound comprising at least one silicon-hydrogen bond. The compound may be, for example, a nonpolymeric compound such as phenyltris(dimethylsiloxy)silane (Formula 3 above), tetrakis(dimethylsiloxy)silane (Formula 4 above), 1,1,3,3-tetraisopropyldisiloxane, 1,1,3,3-tetramethyldisiloxane, 1,1,4,4-tetramethyldisilethane bis(dimethylsilyl)ethane and 1,1,3,3-tetramethyldisilazane; hydride terminated polymeric cross-linkers with different molecular weights, such as hydride-terminated polydimethylsiloxanes (Formula 5 above, wherein q is about 5 to about 1000) including DMS-H03, DMS-H11, DMS-H21, DMS-H25, DMS-H31 and DMS-H41 commercially available from Gelest, hydride terminated polyphenyl-(di-methylhydrosiloxy)siloxanes (Formula 6 below, wherein w is about 5 to about 50) such as HDP-111 commercially available from Gelest, and hydride terminated methylhydrosiloxane-phenylmethylsiloxane copolymers, such as HPM-502 commercially available from Gelest; non-hydride terminated polymeric cross-linkers such as trimethylsiloxy terminated-polymethylhydrosiloxanes and trimethylsiloxy-terminated methylhydrosiloxane-dimethylsiloxane copolymers, such as XL-103, XL-110, XL-111, XL-112, XL-115 and XL-150, commercially available from NuSil, and HMS-013, HMS-031, HMS-082, HMS 151, HMS-301, HMS-991 commercially available from Gelest.

Other Si—H containing compounds may also be used. For example, suitable Si—H containing compounds are known as Hydride Q resins, CAS No. 68988-57-8, also known as "Silicic acid ($H_4SiO_4$), tetraethyl ester, reaction products with chlorodimethylsilane". Such compounds are commercially available from Gelest as HQM-105 and HQM-107, illustrated as having the following formula:

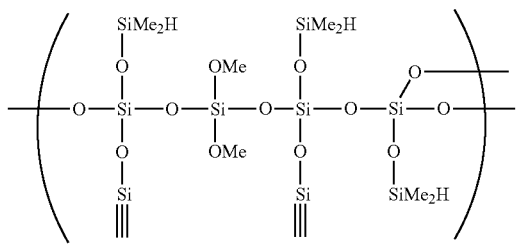

Hydride Q resins commercially available from Gelest, as HQM-105 and HQM-107, may have a viscosity of from 3-8 cSt. (e.g., 3-5 cSt. for HQM-105 and 6-8 cSt. for HQM-107), a hydride equivalent/kilogram of 7.5-9.2 (e.g., 7.8-9.2 for HQM-105 and 7.5-9.0 for HQM-107), an equivalent weight of 110-135 (e.g., 110-130 for HQM-105 and 115-135 for HQM-107), a specific gravity of about 0.90 to about 1.0 (e.g., 0.94 for HQM-105 and 0.95 for HQM-107), and a refractive index of 1.41.

The surface treatment composition may include a relatively low concentration of the silicon-hydride compound, in a suitable solvent. For example, the surface treatment composition may include the silicon-hydride compound in an amount of about 0.01 to about 2.0 wt. %, or about 0.05 wt. % to about 1.0 wt. %. For example, the surface treatment composition may include the silicon-hydride compound in an amount of about 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.3, 1.4, 1.5, 1.6, 1.7, 1.8, 1.9 or 2.0 wt. %.

The surface treatment composition may include the silicone hydride compound in a suitable solvent, such as an organic solvent. For example, the solvent may be methanol, ethanol, isopropanol, n-butanol, tetrahydrofuran, diethyl ether, pentane, hexane, dichloromethane, benzene, toluene, or the like.

The silicone material may be contacted with a surface treatment composition, for example, by contacting the material with the surface treatment composition for a period of time. The period of time may be from about 1 second (sec) to about 60 minutes (min), from about 10 seconds to about 30 minutes, or from about 1 minute to about 10 minutes. For example, the silicone material can be contacted with a surface treatment composition for about 1 sec, 2 sec, 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, 20 sec, 21 sec, 22 see, 23 sec, 24 sec, 25 sec, 26 sec, 27 sec, 28 sec, 29 sec, 30 sec, 31 sec, 32 sec, 33 sec, 34 sec, 35 sec, 36 sec, 37 sec, 38 sec, 39 sec, 40 sec, 41 sec, 42 sec, 43 sec, 44 sec, 45 see, 46 sec, 47 sec, 48 sec, 49 sec, 50 sec, 51 sec, 52 sec, 53 sec, 54 sec, 55 sec, 56 sec, 57 sec, 58 sec, 59 sec, 60 sec, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 Mill, 58 min, 59 min, 60 min. One skilled in the art will appreciate that the contact time will depend on the choice of silicon hydride compound, the amount of silicon hydride compound, and the solvent used for the surface treatment composition.

The surface treated silicone material can be dried, for example, to remove residual solvent. The surface treated silicone material can be dried at a temperature of about 20° C. to about 200° C., or about 100° C. to about 180° C., e.g., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., or about 200° C. The drying may be conducted for about 1 minute (min) to about 24 hours (h), or about 1 min to about 60 min. For example, the drying may be conducted for about 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h.

Following surface treatment, the surface treated silicone material can be treated to remove unreacted starting materials such as residual monomers, oligomers, cross-linkers, additional components such as UV absorbers, or other contaminants. Such treatment may involve extraction with an organic solvent, e.g., using a Soxhlet extraction method. Any suitable organic solvent may be used, including but not limited to methanol, ethanol, isopropanol, acetone, tetrahydrofuran, acetonitrile, methylene chloride and the like. Suitable solvents include ethanol and isopropanol. The surface treated silicone material can be extracted, e.g., using Soxhlet extraction, for about 1 hour to about 10 days, e.g., about 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, or about 2 days, 3 days, 4 days, 5 days, 6 days, 7 days, 8 days or 9 days. Extraction processes (e.g., Soxhlet extraction) can damage certain materials such as silicone materials, and may affect the mechanical and/or optical properties of the silicone materials. The surface treatments of described herein may reduce such damage and may allow the surface treated silicone materials to be extensively extracted without affecting the optical and mechanical properties of the materials.

The surface treated silicone material can be evaluated using standard methods, for example, to determine its compression modulus, its surface tackiness, the refractive index, % transmission using UV-vis, and the like.

For example, the surface treated silicone material may have a compression modulus that is not substantially different from that of the corresponding untreated silicone material. For example, the surface treated silicone material may have a compression modulus that is not more than about 20% greater than that of the corresponding untreated silicone material, or not more than about 19%, 19%, 17%, 16%, 15%, 14%, 13%, 12%, 11%, 10%, 9%, 8%, 7%, 6%, 5%, 4%, 3%, 2% or 1% greater than that of the corresponding untreated silicone material.

The refractive index of the surface treated silicone material may be from about 1.40 to about 1.56, or from about 1.41 to about 1.52. For example, the refractive index may be about 1.40, 1.41, 1.42, 1.43, 1.44, 1.45, 1.46, 1.47, 1.48, 1.49, 1.50, 1.51, 1.52, 1.53, 1.54, 1.55 or 1.56.

The surface treated silicone material may exhibit significantly less surface tackiness than a corresponding untreated silicone material. Tackiness may be evaluated, for example, by determining the load force required to separate a sample from an acetate sheet. Tacky material would be expected to require a high load force to separate the sample from the sheet, while materials with lower tackiness would be expected to require a lower load force. Using such a test, a surface treated silicone material may require a load force of about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% of the load force required to separate an analogous untreated sample.

When evaluated using UV-vis spectroscopy, the percent transmission of a surface treated silicone material may be greater than about 80%, 81%, 82%, 83%, 84%, 85%, 86%, 87%, 88%, 89%, 90%, 91%, 92% 93%, 94%, 95%, 96%, 97%, 98% or 99%, particularly in the visible range of above about 400 nm to about 700 nm, and up to about 1100 nm.

c. Silicone Lenses

The surface treated silicone material may be used as an implantable medical device. Such medical device, by way of example, may be a soft-gel implantable intraocular lens. Embodiments of the present disclosure may also be utilized in other applications or devices where control of surface tackiness is important. For example, the surface treated silicone materials may also be used for contact lenses.

As for IOLs, it is desirable they can be folded, rolled or otherwise deformed such that they can be inserted through small incisions. Furthermore, in order to reduce patient trauma and post-surgical recovery time, the IOL preferably comprises a responsive polymer that unfolds in a controlled manner. To meet these requirements, the polymers preferably have minimal self-tack and do not retain excessive amounts of stored mechanical energy.

Historically, foldable IOL materials have been designed to be tough (tensile strength of greater than 750 pounds per square inch [psi]) and with a relatively high percent elongation (greater than 100%). These properties give the IOL sufficient toughness such that the IOL does not tear from the forces experienced during insertion through a 2.6 to 3.2 mm incision. Presently available foldable IOLs include, among others, Sensar® (Abbott Medical Optics, Santa Ana Calif.), an acrylic IOL having a tensile strength of about 850 psi and an elongation at break of about 140%; SLM-2® (Abbott Medical Optics, Santa Ana Calif.), a silicone IOL having a tensile strength of about 800 psi and an elongation at break of about 230%; and AcrySof® (Alcon Laboratories, Fort Worth, Tex.) having a tensile strength of about 1050 psi. Such IOLs are suitable for insertion through incision sizes of about 2.6 mm or greater.

The polymer materials described herein may be used to form ophthalmic devices and other devices that are soft to very soft and may be foldable.

Flexibility in monomer selection is provided herein, which provides for control over the material's mechanical, optical and/or thermal properties. For example, the ability to adjust a material's refractive index (RI) and mechanical properties is important in designing ultra-small incision IOLs. Also, hydrophobic siloxy materials having excellent ocular biocompatibility are anticipated. Thus, it surprisingly has been discovered that by utilizing the silicone materials according to embodiments of the present invention an IOL optic can be made that has properties permitting passage of the IOL through an ultra-small incision without damage to the IOL, the inserter cartridge, or the eye. In addition, the IOL may have at least one resilient haptic that shares a common siloxy monomer with the optic.

In certain embodiments, silicone materials having unique properties are derived from the inherent flexibility of the siloxane bond. The alternating silicon-oxygen polymer backbone of siloxanes may make them remarkably more flexible than their organic counterparts that have a carbon-oxygen backbone. This property of siloxanes results in low glass-transition temperatures ($T_g$) and excellent flexibility. Furthermore, a low initial modulus is another important attribute of the novel siloxanes. In order to pass through the insertion cartridge, a refractive IOL is desirably capable of elongating up to about 100%. Therefore, it may be important that the initial modulus is at desirable levels. A low initial modulus translates to low stimulus required to express the IOL through the cartridge. Further, when a desired amount of selected siloxanes, cross linkers and catalysts are combined, the resulting material may have the flexibility and modulus required to make, for example, the optic portion of an IOL suitable for insertion through a small incision without harming the IOL, the inserter cartridge, or the eye.

In some embodiments, an intraocular lens comprises an optic and a haptic made from a common polymeric material so that they also have a common refractive index; however, the optic and haptic have mechanical property that is different for each. In some embodiments, the IOL may be formed according to an embodiment so that the optic and haptic have different, moduli of elasticity. For example, an accommodating IOL may be formed so that the optic has a lower modulus than the haptic, thus allowing the relatively stiff haptic to protrude inside the relatively soft optic without causing unwanted reflections due to a refractive index mismatch at interfaces between the optic and the protruding haptic. Examples of accommodating IOLs having a stiffer protruding haptic are disclosed in co-pending U.S. patent application Ser. Nos. 11/618,411, 11/618,325, and 11/864,450, which are herein incorporated by reference in their entirety.

One way to adjust moduli between the haptic and optic may be provided by an adjustment in the amount of cross-linker and/or catalyst and/or MVC content of each IOL component. Embodiments herein may be used to provide IOLs in which at least the optic thereof has a modulus that is less than about 100 kPa, less than 75 kPa, or even less than 50 kPa or 25 kPa. The stiffness of the haptic may be greater than 500 kPa, or greater than 3000 kPa, depending on the particular design requirements. In some embodiments, the modulus of the haptic is greater than that of the optic by at least 50%, by at least 150%, by at least 250%, or by at least 500%. In some embodiments, the modulus may vary continuously over at least some interface regions between the haptic and the optic, for example, to provide a particular performance or stress distribution over the IOL in reaction to an external force on the IOL (e.g., an ocular force produced by the capsular bag, zonules, or ciliary muscle of an eye into which the IOL is inserted).

In some embodiments, an ophthalmic lens, such as an intraocular lens, comprises an optic having a clear aperture that comprises an inner portion and an outer portion disposed about said inner portion. The inner portion and outer portion comprise a common polymeric material and may have a common refraction index; however, the inner portion has a modulus that is different from that of the outer portion. The difference in modulus may be selected, for example, to control the amount and/or form of deformation of the optic in reaction to an external force such as an ocular force produced by the capsular bag, the zonules, and/or the ciliary muscle of an eye into which the optic is placed. In some embodiments, the refractive index may also vary between the zones, for example, to control aberrations of the optic in a stressed or unstressed state.

The modulus of the inner portion of the optic may by greater than or less than that of the outer portion, depending of the particular design requirements. In some embodiments, the optic comprises three or more zones disposed within the clear aperture of the optic. In other embodiments, the modulus of at least portions of the optic may vary continually, for example, by producing a catalyst gradient throughout a polymeric fluid used to form the optic. In some embodiments, the zones of the optic may have an ellipsoid or similar shape, such that the modulus varies from the center of the optic outward in a three-dimensional manner. Alternatively or additionally, the variation in modulus of the zones may vary in a two dimensional manner, for example, forming concentric rings as the modulus varies in radial direction from the optical axis of the optic. The difference in modulus between two zones of the optic may be greater than or equal to 5%, or greater than or equal to 15%, or greater than or equal to 25%, or greater than or equal to 50%, depending on the number of zones and the desired performance of the optic under a given loading force.

Some embodiments may provide a relatively low modulus material that is particularly suitable for use in at least the optic of an accommodating IOL. For example, an adjustment in the amount of cross-linker, number of vinyl terminations, number of vinyl pendent groups, catalyst and/or MVC content, the haptic portion of an IOL or accommodating IOL may be made. Controlling these variables allows silicone fluids of different refractive indices, viscosities and vinyl functionality to be prepared. Embodiments may be used to provide IOL's in which at least the optic thereof has a modulus that is less than about 100 kPa, less than 75 kPa, or even less than 50 kPa or 25 kPa.

The materials made may have low initial moduli and a low glass transition temperature ($T_g$). Moreover, the IOLs may be multifocal (either refractive or diffractive), accommodating (e.g., deformable or movable under the normal muscle movements of the human eye), highly biocompatible and have RIs ranging from about 1.40 to about 1.56, preferably from about 1.41 to about 1.52, for light in the visible wavelengths. These and other objects described herein may be achieved by providing an unsaturated terminated silicone fluid and cross-linking it using a hydride cross-linking agent and catalyst (e.g., a platinum catalyst). The unsaturated terminated silicone fluid, in some embodiments, can have more than three vinyl terminations. In different embodiments, the unsaturated terminated silicone fluid can have two, three, four, five or six vinyl terminations. In another embodiment, metals aside from platinum, more preferably transition metals, may be used. Herein, silicone fluids are disclosed that may be cross-linked to prepare polymers with different moduli.

The present invention has multiple aspects, illustrated by the following non-limiting examples.

3. Examples

Example 1

Preparation of Silicone Material

A silicone material with a refractive index (RI) of 1.47±0.01 was prepared by mixing a hexavinyl-terminated diphenylsiloxane-dimethylsiloxane copolymer silicone fluid of DP (degree of polymerization) 600 (comprising 15.8% diphenylsiloxane units and 83.9% dimethylsiloxane units), with a platinum carbonyl cyclovinylmethylsiloxane complex, and phenyltris(dimethylsiloxy)silane and Hydride Q resin (HQM-107 from Gelest) cross-linkers to form a silicone mixture. The silicone mixture was then poured into a mold and cured at 150° C. for 10 minutes, resulting in a soft silicone gel with clear appearance.

The initial modulus of this set silicone gel was 39 kPa. After 5 days of extensive Soxhlet extraction with isopropanol, the modulus of this set of discs was 51 kPa. The weight loss was approximately 12% after the extraction process. However, the disc became hazy after Soxhlet extraction, rendering it unsuitable for use in ophthalmologic devices, such as IOLs.

Example 2

Preparation and Characterization of Surface Treated Silicone Discs

Silicone discs prepared according to Example 1 (without a Soxhlet extraction step) were placed in a 0.5% HQM-107 solution in isopropanol for a specific period of time, such as from 10 to 60 seconds. These treated discs were then taken out from the solution and dried in a 150° C. oven for 10 minutes to remove any residual solvent.

Figure 2:
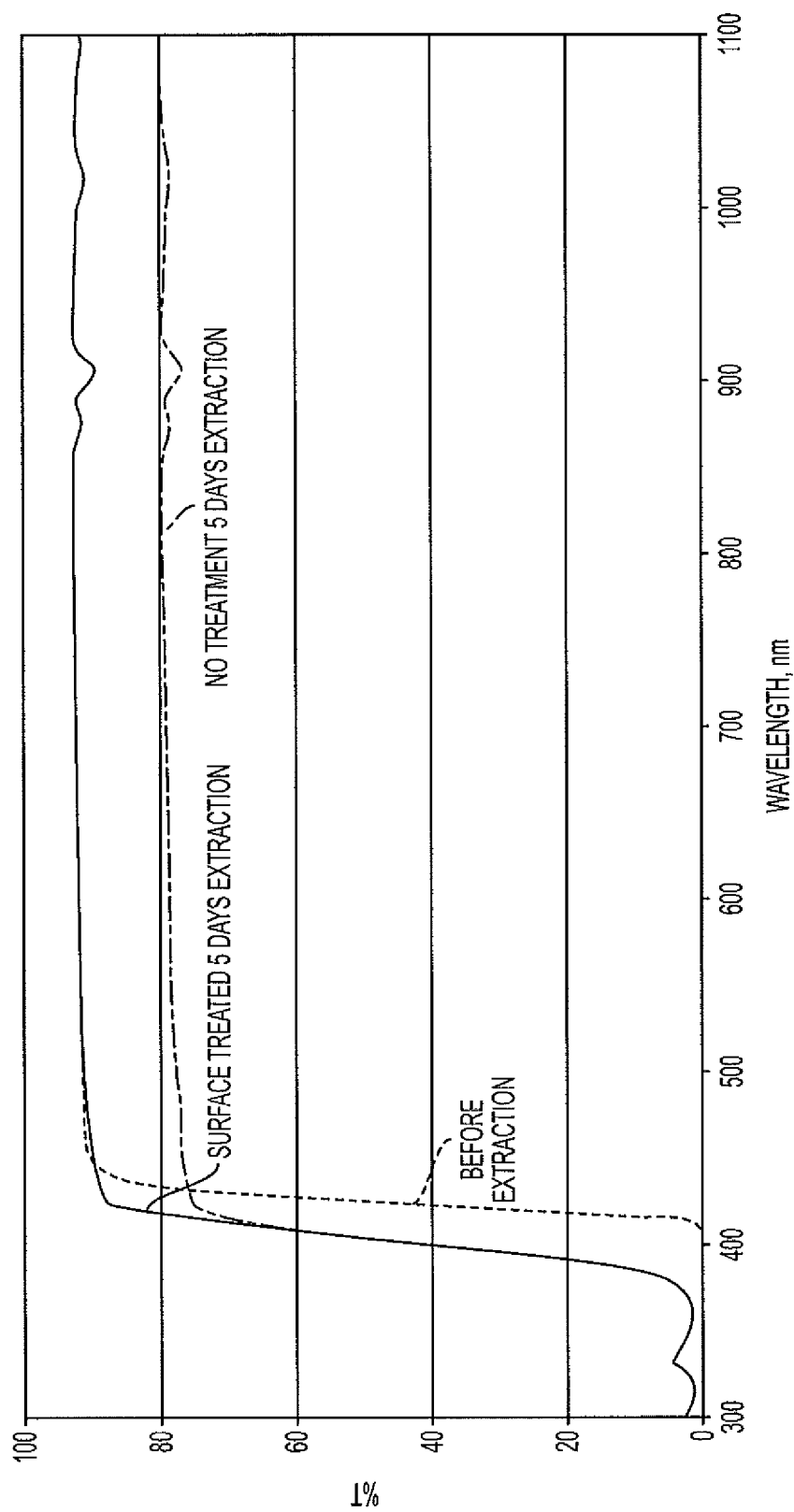
FIG. 2 shows a graph of percent transmission in a UV-vis scan of discs with or without a surface treatment as described herein, before and after extraction.

Samples after these treatments remained clear after extensive Soxhlet extraction with isopropanol. FIG. 1 shows the discs after 5 days of extraction for samples with surface treatment (60 seconds, right disc) and without surface treatment (left disc). The treated disc remained clear with surface treatment, but the untreated disc became opaque after extensive extraction. FIG. 2 shows the percent transmission (% T) in a UV-vis scan of the discs before and after extraction, for samples with and without surface treatment. The percent transmission (% T) above 400 nm was almost the same before and after extraction for samples with the surface treatment, while the % T above 400 nm was significantly lower for the sample without treatment.

Compression moduli of the discs before and after extraction were measured using a Q800 DMA (TA Instruments) Diameter and thickness of the sample was measured using a calibrator. A comparator could also be used. After loading the sample on the holder, the temperature of the system was raised to 35° C. and held at equilibrium for 5 minutes before testing. R amp force was applied to the disc at 1 N/min to the maximum of 9 N/min. The modulus was determined by the slope of two elongation points (4% and 8%) from the curve. Percent weight loss was also measured after five days of Soxhlet extraction with isopropanol. As shown in Table 1, the compression modulus increased slightly following the surface treatment, but remained relatively stable following extensive Soxhlet extraction. However, the percent weight loss was significantly reduced for all samples following various treatment times.

TABLE 1

Compression Moduli and Weight Loss
Before and After Surface Treatment

| Treatment time | Control | 10 seconds | 30 seconds | 60 seconds |
|---|---|---|---|---|
| Initial modulus (kPa) | 39 ± 0 (N = 2) | 47 ± 0 (N = 2) | 47 ± 1 (N = 2) | 53 ± 1 (N = 4) |
| Modulus after 5 Days Soxhlet Extraction (kPa) | 51 ± 0 (N = 2) | 53 ± 2 (N = 2) | 53 ± 1 (N = 2) | 57 ± 2 (N = 4) |
| % weight loss | 12.4 | 7.8 | 8.1 | 6.8 ± 0.6 (N = 2) |

Prior to extraction, the tackiness of the silicone discs were evaluated using a test method developed in-house. Tackiness was characterized by the load force required to separate the sample and an acetate sheet. Tacky material had a high load force while material with lower tackiness had a lower load force. Table 2 shows the maximum force (gf) required to separate the silicone materials from the acetate sheet, for samples without treatment and samples treated for different time periods. The data demonstrate that the force required to separate the control sample (without surface treatment) was significantly higher than that for samples that were subjected to the different surface treatment conditions. The separation force was very similar for samples treated anywhere from 10 to 60 seconds.

TABLE 2

Tackiness Test Results

| Treatment time | Control | 10 seconds | 30 seconds | 60 seconds |
|---|---|---|---|---|
| Max. force (gf) | 64.8 | 22.8 | 20.7 | 23.6 |

Example 3

Preparation and Characterization of Surface Treated Silicone Discs

Silicone discs prepared according to Example 1 were placed in a 0.5% HQM-107 solution for a specific period of time, such as from 1 minute to 60 minutes. These treated discs were then taken out from the solution and dried in a 150° C. oven for 10 minutes to remove any residual solvent.

Compression moduli of the discs were measured as described in Example 2, and the percent weight loss was measured after five days of Soxhlet extraction with isopropanol. As shown in Table 3, the compression modulus increased with treatment time. Additionally, discs subjected to long treatment times experienced cracking after 5-day Soxhlet extraction with isopropanol, and the weight loss and compression modulus could not be measured.

TABLE 3

Compression Moduli and Weight Loss
Before and After Surface Treatment

| Treatment time | Control | 1 minute | 10 minutes | 60 minutes |
|---|---|---|---|---|
| Initial modulus (kPa) | 41 ± 1 (N = 2) | 52 ± 1 (N = 2) | 64 ± 1 (N = 2) | 98 ± 9 (N = 2) |
| Modulus after 5 Days Soxhlet Extraction (kPa) | 50 + 0 (N = 2) | 60 ± 2 (N = 2) | 69 ± 1 (N = 2) | Crack |
| % weight loss | 16.5 | 9.7 | 5.5 | NA |

Tackiness was evaluated as described in Example 2, and data are illustrated in Table 4. The force required to separate the control sample (without surface treatment) was significantly higher than that for surface-treated samples.

TABLE 4

Tackiness Test Results

| Treatment time | Control | 1 minute | 10 minutes | 60 minutes |
|---|---|---|---|---|
| Max. force (gf) | 59.6 | 19.7 | 22.7 | NA |

Example 4

Preparation and Characterization of Surface Treated Silicone Discs

Silicone discs prepared according to Example 1 were placed in a 0.5% HQM-107 solution for one minute. These treated discs were then taken out from the solution and dried in a under different conditions.

Compression moduli of the discs were measured as described in Example 2, and the percent weight loss was measured after five days of Soxhlet extraction with isopropanol. As evidenced by the data shown in Table 5, the shorter drying times at higher temperatures may be desired.

TABLE 5

Compression Moduli and Weight Loss Before and After Surface Treatment

| | | Drying conditions | | |
|---|---|---|---|---|
| | Control | 60° C., 24 hours | 100° C., 10 minutes | 150° C., 10 minutes |
| Initial modulus (kPa) | 45 | 60 ± 1 (N = 2) | 55 ± 1 (N = 2) | 55 ± 1 (N = 2) |
| Modulus after 5 Days Soxhlet Extraction (kPa) | 52 | 66 ± 3 (N = 2) | 63 ± 1 (N = 2) | 64 ± 0 (N = 2) |
| % weight loss | 15.9 | 9.5 | 8.8 | 8.8 |

Tackiness was evaluated as described in Example 2, and data are illustrated in Table 6. The force required to separate the control sample (without surface treatment) was significantly higher than that for surface-treated samples. Separation forces were similar for the treated samples.

TABLE 6

Tackiness Test Results

| | | Drying conditions | | |
|---|---|---|---|---|
| | Control | 60° C., 24 hours | 100° C., 10 minutes | 150° C., 10 minutes |
| Max. force (gf) | 69.5 | 30.9 | 27.0 | 23.2 |

Example 5

Preparation and Characterization of Surface Treated Silicone Discs

A silicone material with a refractive index (RI) of 1.47±0.01 was prepared by mixing a hexavinyl-terminated diphenylsiloxane-dimethylsiloxane copolymer silicone fluid of DP (degree of polymerization) 600 (comprising 15.8% diphenylsiloxane units and 83.9% dimethylsiloxane units), with 0.25% platinum carbonyl cyclovinylmethylsiloxane complex, and phenyltris(dimethylsiloxy)silane and Hydride Q resin (HQM-107 from Gelest) cross-linkers to form a silicone mixture. Formula I in Table 7 (F1) had a hydride:vinyl ratio of 0.6 and was heat pretreated for 4 hours at 130° C.; formula 2 (F2) had a hydride:vinyl ratio of 0.4 and was not subject to a heat pretreatment; and formula 3 (F3) had a hydride:vinyl ratio of 0.6 and was subject to a heat pretreatment for 12 hours at 130° C.

The silicone mixtures was then poured into a mold and cured at 150° C. for 10 minutes, resulting in a soft silicone gel with clear appearance.

Silicone discs prepared as above were placed in a 0.5% HQM-107 solution in isopropanol for 60 seconds. These treated discs were then taken out from the solution and dried in a 150° C. oven for 10 minutes to remove any residual solvent.

Compression moduli were determined as described in Example 1. Data are illustrated in Table 7.

TABLE 7

Compression Moduli and % Extractables and After Surface Treatment

| | F1 | | F2 | | F3 | |
|---|---|---|---|---|---|---|
| Property | Untreated | Treated | Untreated | Treated | Untreated | Treated |
| Initial modulus (kPa) | 47 ± 0 (N = 2) | 57 ± 1 (N = 2) | 44 ± 1 (N = 2) | 58 ± 2 (N = 6) | 26 ± 1 (N = 2) | 34 ± 1 (N = 4) |
| Modulus after 5 Days Soxhlet Extraction (kPa) | 60 ± 3 (N = 2) | 65 ± 2 (N = 5) | 52 ± 0 (n = 2) | 66 ± 3 (n = 4) | 38 ± 1 (N = 4) | 39 ± 1 (N = 2) |
| % Extractable | 16.9 | 10.5 ± 0.5 (N = 3) | 15.0 | 10.3 ± 2.5 (N = 2) | 20.6 | 11.6 |

Silicone discs prepared as above were subjected to different surface treatment conditions, for example with varying concentrations of the HQM-107, and using different solvents. All discs were dried for 10 minutes at 150° C., and compression moduli were determined as described in Example 1. Results are illustrated in Table 8.

TABLE 8

Compression Moduli After Surface Treatment

| | Solvent = Hexane Initial Modulus (kPa) | Solvent = Methanol Initial Modulus (kPa) |
|---|---|---|
| Non-coated | 36 ± 2 (N = 4) | 35 ± 2 (N = 4) |
| 0.5% HQM-107 | 56 ± 3 (N = 2) | 43 ± 1 (N = 2) |
| 1.0% HQM-107 | 62 ± 4 (N = 2) | 46 ± 3 (N = 2) |
| 2.0% HQM-107 | 66 ± 0 (N = 2) | 47 ± 1 (N = 2) |

Silicone discs prepared as above were subjected to different surface treatment conditions, using phenyltris(dimethylsiloxy)silane in isopropanol as the silicon-hydride compound for 5 seconds. All discs were dried for 10 minutes at 150° C., and compression moduli were determined as described in Example 1. Results are illustrated in Table 9.

TABLE 9

Compression Moduli and % Extractables and After Surface Treatment

|  | Initial Modulus (kPa) | Modulus after 5 Days Soxhlet Extraction (kPa) | % Weight Loss |
|---|---|---|---|
| Non-coated | 44 ± 0 (N = 2) | 52 ± 0 (N = 2) | 15.04% |
| 10 seconds | 51 ± 4 (N = 2) | 57 ± 1 (N = 2) | 10.04% |
| 30 seconds | 57 ± 0 (N = 2) | 58 ± 8 (N = 2) | 7.59% |
| 60 seconds | 58 ± 2 (N = 2) | 66 ± 3 (N = 4) | 10.23% (N = 2) |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A surface treated intraocular lens, comprising:
   a) the product of a reaction mixture comprising a platinum catalyst, a silicon-hydride cross-linker, and a polymer having formula (I):

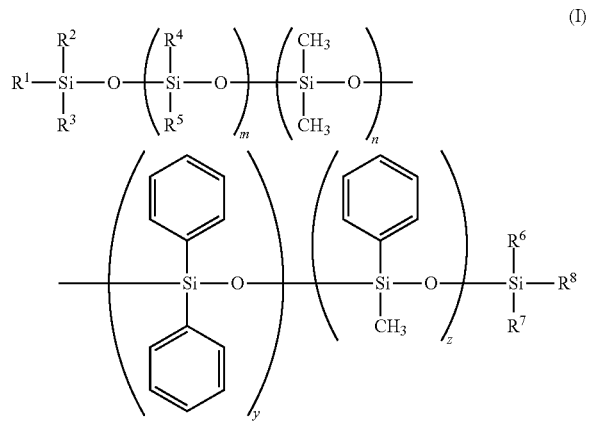

wherein:
the sum of m and n is x;
x is from 0 to about 5000;
y is from 0 to about 500;
z is from 0 to about 500;
the sum of x, y, and z is at least 1;
$R^1$-$R^8$ are each independently selected from the group consisting of hydrogen, —$CH_3$, —$C_6H_5$ and —CH=$CH_2$;
wherein at least one of $R^1$, $R^2$ and $R^3$ is —CH=$CH_2$;
wherein at least one of $R^6$, $R^7$, or $R^8$ is —CH=$CH_2$; and
   b) a surface treatment consisting essentially of a compound comprising at least one Si—H bond.

2. The lens of claim 1, wherein in is 0 and z is 0.

3. The lens of claim 1, wherein the polymer has a mole ratio of diphenylsiloxane monomer units of about 0.10 to about 0.20, and a mole ratio of dimethylsiloxane units of about 0.80 to about 0.90.

4. The lens of claim 1, wherein $R^1$, $R^2$, $R^3$, $R^6$, $R^7$, and $R^8$ are each —CH=$CH_2$.

5. The lens of claim 1, wherein the cross-linker is selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin, (silicic acid ($H_4$ $SiO_4$), tetraethyl ester, reaction products with chlorodimethylsilane), and a mixture of any thereof.

6. The lens of claim 1, wherein the surface treatment consists essentially of a compound selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin (silicic acid ($H_4$ $SiO_4$), tetraethyl ester, reaction products with chlorodimethylsilane), and a mixture of any thereof.

7. The lens of claim 6, wherein the surface treatment consists essentially of a hydride Q resin (silicic acid ($H_4SiO_4$), tetraethyl ester, reaction products with chlorodimethylsilane).

8. A method for manufacturing a surface treated intraocular lens, comprising:
   a) providing a reaction mixture comprising:
      (i) a polymer having formula (I):

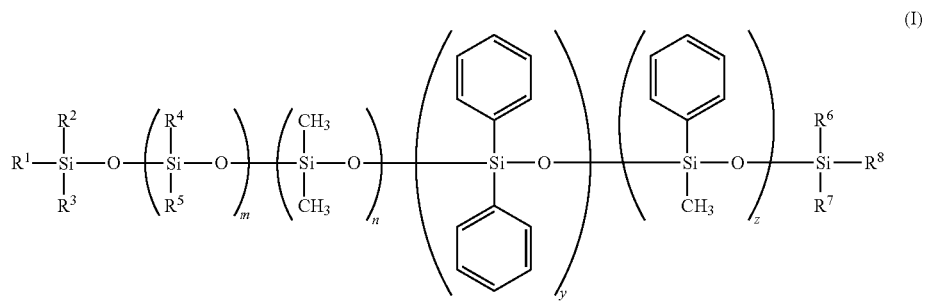

wherein:
the sum of m and n is x;
x is from 0 to about 500;
y is from 0 to about 500;
z is from 0 to about 500;
the sum of x, y, and z is at least 1;
R$^1$-R$^8$ are each independently selected from the group consisting of hydrogen, —CH$_3$, —C$_6$H$_5$ and —CH=CH$_2$;
wherein at least one of R$^1$, R$^2$ and R$^3$ is —CH=CH$_2$;
wherein at least one of R$^6$, R$^7$, or R$^8$ is —CH=CH$_2$;
(ii) a silicon hydride cross-linker; and
(iii) a platinum catalyst;
b) curing the reaction mixture to provide a cured silicone material;
c) surface treating the cured silicone material with a surface treatment composition consisting essentially of a compound comprising at least one Si—H bond to provide a surface treated silicone material; and
d) drying the surface treated silicone material to provide the surface treated intraocular lens.

9. The method of claim 8, wherein m is 0 and z is 0.

10. The method of claim 8, wherein the polymer has a mole ratio of diphenylsiloxane monomer units of about 0.10 to about 0.20, and a mole ratio of dimethylsiloxane units of about 0.80 to about 0.90.

11. The method of claim 8, wherein R$^1$, R$^2$, R$^3$, R$^6$, R$^7$, and R$^8$ are each —CH=CH$_2$.

12. The method of claim 8, wherein the cross-linker is selected from the group consisting of phenyltris(dimethylsiloxy)silane, 1,1,3,3-tetraisopropyldisiloxane, 1,1,3,3,-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin (silici acid (H$_4$SiO$_4$), tetraethyl ester, reaction products with chlorodimethylsilane), and a mixture of any thereof.

13. The method of claim 8, wherein the surface treatment composition consists essentially of a compound selected from the group consisting of phenyltris(dimethylsiloxy)silane, 1,1,3,3-tetraisopropyldisiloxane,1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin (silici acid (H$_4$SiO$_4$), tetraethyl ester, reaction products with chlorodimethylsilane), and a mixture of any thereof.

14. The method of claim 13, wherein the surface treatment composition consists essentially of a hydride Q resin (silici acid (H$_4$SiO$_4$), tetraethyl ester, reaction products with chlorodimethylsilane).

15. The method of claim 8, wherein the surface treating step comprises contacting the cured silicone material with the surface treatment composition for about 10 seconds to about 10 minutes.

16. The method of claim 8, wherein the drying step comprises drying the surface treated silicone material for about 1 minute to about 60 minutes.

17. The method of claim 8, wherein the surface treated silicone material is dried at a temperature of about 100° C. to about 180° C.

18. The method of claim 8, further comprising a step of extracting the cured silicone product with an organic solvent, between steps c) and d).

19. The method of claim 18, wherein the extracting step comprises Soxhlet extraction.

20. The method of claim 17, wherein the organic solvent is selected from the group consisting of ethanol and isopropanol.

21. An intraocular lens prepared by a process comprising the steps of:
a) providing a reaction mixture comprising:
(i) a polymer having formula (I):

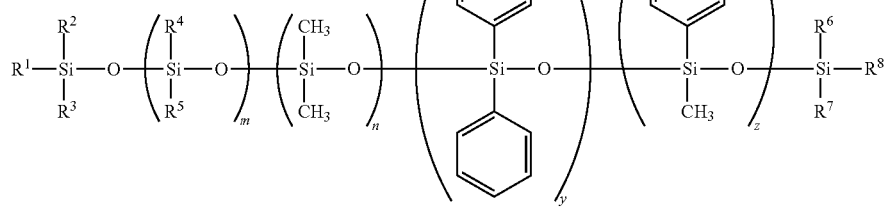

wherein:
the sum of m and n is x;
x is from 0 to about 5000;
y is from 0 to about 500;
z is from 0 to about 500;
the sum of x, y, and z is at least 1;
R$^1$-R$^8$ are each independently selected from the group consisting of hydrogen, —CH$_3$, —C$_6$H$_5$ and —CH=CH$_2$;
wherein at least one of R$^1$, R$^2$ and R$^3$ is —CH=CH$_2$;
wherein at least one of R$^6$, R$^7$, or R$^8$ is —CH=CH$_2$;
(ii) a silicon hydride cross-linker; and
(iii) a platinum catalyst;
b) curing the reaction mixture to provide a cured silicone material;
c) surface treating the cured silicone material with a surface treatment composition consisting essentially of a compound comprising at least one Si—H bond to provide a surface treated silicone material; and
d) drying the surface treated silicone material.

22. The lens of claim 21, wherein m is 0 and z is 0.

23. The lens of claim 21, wherein the polymer has a mole ratio of diphenylsiloxane monomer units of about 0.10 to about 0.20, and a mole ratio of dimethylsiloxane units of about 0.80 to about 0.90.

24. The lens of claim 21, wherein $R^1$, $R^2$, $R^3$, $R^6$, $R^7$, and $R^8$ are each —CH=CH$_2$.

25. The lens of claim 21, wherein the cross-linker is selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride terminated methylhydrosiloxane-phenylmethylsiloxane copolymer, and a hydride Q resin (silici acid (H$_4$SiO$_4$), tetraethyl ester, reaction products with chlorodimethylsilane), and a mixture of any thereof.

26. The lens of claim 21, wherein the surface treatment composition consists essentially of a compound selected from the group consisting of phenyltris(dimethylsiloxy)silane, 1,1,3,3-tetraisopropyldisiloxane, 1,1,3,3-tetramethyldisiloxane, 1,1,4,4-tetramethyldisilethane, bis(dimethylsilyl)ethane, 1,1,3,3-tetramethyldisilazane, tetrakis(dimethylsiloxy)silane, a hydride-terminated polyphony-(dimethylhydrosiloxy)siloxane, a hydride terminated polydimethylsiloxane, a hydride-terminated methylhydrosiloxane-phenylmethylsiloxane copolymer, and a hydride Q resin (silici acid (H$_4$SiO$_4$), tetraethyl ester, reaction products with chlorodimethylsilane), and a mixture of any thereof.

27. The lens of claim 26, wherein the surface treatment composition consists essentially of a hydride Q resin (silici acid (H$_4$SiO$_4$), tetraethyl ester, reaction products with chlorodimethylsilane).

28. The lens of claim 21, wherein the surface treating step comprises contacting the cured silicone material with the surface treatment composition for about 10 seconds to about 10 minutes.

29. The lens of claim 21, wherein the drying step comprises drying the surface treated silicone material for about 1 minute to about 60 minutes.

30. The lens of claim 21, wherein the surface treated silicone material is dried at a temperature of about 100° C. to about 180° C.

31. The lens of claim 21, further comprising a step of extracting the surface treated silicone material with an organic solvent, between steps c) and d).

32. The lens of claim 31, wherein the extracting step comprises Soxhlet extraction.

33. The lens of claim 31, wherein the organic solvent is selected from the group consisting of ethanol and isopropanol.

* * * * *